United States Patent [19]

Koprowski et al.

[11] Patent Number: 4,847,423

[45] Date of Patent: Jul. 11, 1989

[54] HYDROFORMYLATION OF AQUEOUS FORMALDEHYDE USING A RHODIUM-TRICYCLOHEXYLPHOSPHINE CATALYST SYSTEM

[75] Inventors: Robert J. Koprowski, Chesapeake, Va.; Jerry D. Unruh, Corpus Christi, Tex.

[73] Assignee: Hoechst Celanese Corporation, Somerville, N.J.

[21] Appl. No.: 163,450

[22] Filed: Mar. 3, 1988

[51] Int. Cl.$^4$ .............................................. C07C 45/50
[52] U.S. Cl. ............................................................. 568/462
[58] Field of Search ............................... 568/462, 862

[56] References Cited

U.S. PATENT DOCUMENTS

| | | | |
|---|---|---|---|
| Re. 32,084 | 2/1986 | Goetz | 568/462 |
| 4,200,765 | 4/1980 | Goetz | 568/862 |
| 4,382,148 | 5/1983 | Drent | 568/462 |
| 4,405,814 | 9/1983 | Carroll et al. | 568/462 |
| 4,414,421 | 11/1983 | Drentz | 568/462 |
| 4,496,781 | 1/1985 | Jacobson et al. | 568/862 |
| 4,503,260 | 3/1985 | Auvil et al. | 568/462 |
| 4,560,806 | 12/1985 | Jacobson | 568/462 |
| 4,605,781 | 8/1986 | Tau | 568/454 |
| 4,625,068 | 11/1986 | Young | 568/454 |
| 4,642,388 | 2/1987 | Young | 568/454 |

OTHER PUBLICATIONS

"Rhodium-Catalyzed Hydroformylation of Formaldehyde", Chan et al., *Journal of Molecular Catalysis*, 19 (1983), pp. 377-391.

"Specific Rate Enhancement by Alkylphosphines in a Homogeneous Rhodium Complex–Catalyzed Hydrogenation of Carbon Monoxide to Ethylene Glycol", Tanaka et al. *Journal of Organometallic Chemistry*, 312 (1986), pp. C71–C74.

"A New Catalyst for the Direct Synthesis of Ethylene Glycol from Carbon Monoxide and Hydrogen", Tamura et al., *Journal of Organometallic Chemistry*, 312 (1986), pp. C75–C78.

"A Novel Rhodium-Tri-N-Alkylphosphine Catalyst System for the Hydrogenation of Carbon Monoxide, Formaldehyde, and Glycolaldehyde", Watanabe et al, *The Chemical Society of Japan, Chemistry Letters*, (1986), pp. 285–288.

"Hydroformylation of Formaldehyde to Give Glycolaldehyde with Halide-Promoted $Rh_4(CO)_{12}$", Marchionna et al., *Journal of the Chemical Society, Chemical Communications*, 1987, pp. 1097–1098.

*Primary Examiner*—Werren B. Lone
*Attorney, Agent, or Firm*—Stuart D. Frenkel

[57] ABSTRACT

Aqueous formaldehyde is hydroformylated to glycol aldehyde in the presence of a rhodium-phosphine ligand complex catalyst in which the phosphine ligand is a trialkyl- or tricycloalkylphosphine and has a specified cone angle. A preferred phosphine ligand is tricyclohexylphosphine.

22 Claims, No Drawings

4,847,423

HYDROFORMYLATION OF AQUEOUS FORMALDEHYDE USING A RHODIUM-TRICYCLOHEXYLPHOSPHINE CATALYST SYSTEM

BACKGROUND OF THE INVENTION

1. Field of the Invention

This invention is related to a process and accompanying catalyst for the preparation of glycol aldehyde and, more particularly, is related to the preparation of glycol aldehyde from the reaction of aqueous formaldehyde, carbon monoxide and hydrogen in the presence of rhodium-phosphine complex catalysts.

2. Description of the Prior Art

Glycol aldehyde is a valuable intermediate in many organic reactions, and is particularly useful as an intermediate in the production of ethylene glycol through a catalytic hydrogenation process.

Ethylene glycol is a valuable commercial chemical with a wide variety of uses, e.g., as a coolant and anti-freeze, monomer for polyester production, solvent, and an intermediate for production of commercial chemicals.

The reaction of formaldehyde with carbon monoxide and hydrogen in the presence of a variety of catalysts at elevated temperatures and superatmospheric pressures is a well known reaction and yields glycol aldehyde, together with methanol, as well as lesser amounts of polyhydroxy compounds which can be subsequently separated by proper separation procedures. For example, U.S. Pat. No. 2,451,333 describes the reaction of formaldehyde, carbon monoxide and hydrogen over a cobalt catalyst to produce ethylene glycol. U.S. Pat. No. 3,920,753 discloses the production of glycol aldehyde by the reaction of formaldehyde, carbon monoxide and hydrogen in the presence of a cobalt catalyst under controlled reaction conditions; however, the process produces relatively low yields of product. European Pat. No. 002,908 describes a process for the production of glycol aldehyde from the reaction of formaldehyde, in the presence of a rhodium-triphenyl phosphine ligand catalyst, with carbon monoxide and hydrogen, in a tertiary amide solvent.

European patent Application 82/200,272.1 describes a process for the preparation of glycol aldehyde which comprises reacting formaldehyde, hydrogen and carbon monoxide in the presence of either a rhodium or cobalt containing catalyst precursor, together with a strong protonic acid, a tertiary amide solvent and a triaryl phosphine.

U.S. Pat. No. 4,200,765 describes a process of preparing a glycol aldehyde involving reacting formaldehyde, carbon monoxide, and hydrogen in a tertiary amide solvent in the presence of a catalytic amount of rhodium in complex combination with carbon monoxide, using triphenyl phosphine as the preferred catalyst promoter. The phosphine-containing catalysts can be prepared by employing suitable phosphine ligands other than triphenyl phosphine. Among a long list of such suitable phosphine ligands is included tricyclohexylphosphine. The sources of formaldehyde used in the process as disclosed in the patent are typical of those commonly used in the technology and include paraformaldehyde, methylal, formalin solutions and polyoxymethylenes. Paraformaldehyde is preferred since the best results are obtained therewith. Also disclosed are solutions of formaldehyde in solvents such as solutions of formaldehyde in aqueous reaction solvent, such as N-methyl pyrrolidin-2-one.

The art relative to the hydroformylation of formaldehyde to glycol aldehyde has preferred to use paraformaldehyde as the formaldehyde source in view of the improved yields which are obtained. The use of aqueous formaldehyde as the formaldehyde source has not yielded sufficient conversion or selectivity to glycol aldehyde. Further, the hydroformylation of aqueous formaldehyde has resulted in deactivation of the rhodium catalyst and as well excessive condensation of glycol aldehyde with formaldehyde and other aldehydes to form higher molecular weight high-boiling sugar-like by-products. The condensation is an aldol-type reaction with becomes more severe at higher temperature and in more basic medium.

Economically, it would be preferable to utilize aqueous formaldehyde as the formaldehyde source in the hydroformylation thereof to glycol aldehyde. It is, thus, a primary objective of the present invention to provide a reaction system which will allow the hydroformylation of aqueous formaldehyde to give glycol aldehyde with sufficient selectivity and without the disadvantageous catalyst deactivation and sugar by-product formation attendant in prior art reaction systems.

SUMMARY OF THE INVENTION

The foregoing and additional objects are accomplished by the present invention which in one of its aspects is a process for selectively producing glycol aldehyde by selectively hydroformylating aqueous formaldehyde, which process comprises contacting in a hydroformylation zone aqueous formaldehyde with carbon monoxide and hydrogen in the presence of a triorganophosphine ligand-stabilized rhodium catalyst wherein a specified triorganophosphine ligand is used. The rhodium complex catalyst has the empirical formula: $RhH_m(CO)_nL_p$ wherein "Rh" is rhodium, "H" is hydrogen, "CO" is carbon monoxide and "L" is a triorganophosphine ligand, and wherein m is 0, 1 or 3, n is from 1 to 3, and p is 1 or 2, the sum of m, n and p being from 3 to 6, said triorganophosphine ligand being selected from the group consisting of trialkylphosphines, including tricycloalkylphosphines, wherein each of the three alkyl, including cycloalkyl groups are alike or different, and each contains from 1 to 10 carbon atoms, and wherein said triorganophosphine ligand has a cone angle within the range of 159 to 171 degrees.

DETAILED DESCRIPTION OF THE INVENTION

The hydroformylation of formaldehyde in the presence of a rhodium complex catalyst to produce glycol aldehyde is well known and there is a large body of prior art pertaining thereto. The description herein will be limited mainly to those process limitations and catalyst limitations to be observed in order to accomplish the high selectivity and high conversion desired. In other words, unless otherwise specified herein conventional hydroformylation conditions and procedures may be utilized.

The source of formaldehyde for use in the present process is aqueous formaldehyde. Aqueous formaldehyde is typically known in the art as formalin which comprises aqueous 37 to 50% solutions of formaldehyde.

In the prior art processes, the hydroformylation of aqueous formaldehyde to glycol aldehyde has not been readily successful. As previously explained, yield and selectivity to glycol aldehyde have been substantially below those achieved utilizing paraformaldehyde as the formaldehyde source. Catalyst deactivation and the formation of sugar-like by-products has also been the disadvantageous result of hydroformylating aqueous formaldehyde in the presence of rhodium-triorganophosphine complex catalysts. The present invention, however, is based on the discovery that aqueous formaldehyde can be hydroformylated to glycol aldehydes at glycol aldehyde selectivities of greater than 80% by utilizing a specific rhodium-phosphine ligand catalyst complex which, although known to the art, has not been specifically suggested for use in the hydroformylating of aqueous formaldehyde and which besides yielding the high selectivity to glycol aldehyde is not deactivated by the formaldehyde reactant and does not result in any appreciable levels of sugar by-product formation.

The catalyst utilized in the present invention is a rhodium complex catalyst of the empirical formula:

$$RhH_m(CO)_nL_p \qquad (I)$$

wherein "Rh" is rhodium, "H" is hydrogen, "CO" is carbon monoxide and "L" is a triorganophosphine ligand, and wherein m is 0, 1 or 3, n is from 1 to 3, and p is 1 or 2, the sum of m, n and p being from 3 to 6. The triorganophosphine ligand must be one selected from the group consisting of trialkylphosphines, including tricycloalkylphosphines, wherein each of the three alkyl (including cycloalkyl) groups are alike or different (but preferably alike) and each contains from 1 to 10 carbon atoms. The triorganophosphine ligand must be one wherein the cone angle is within the range of 159 to 171 degrees.

While the prior art literature discloses the general class of rhodium complex catalysts listed above, the prior art was generally concerned with preparation of glycol aldehyde from paraformaldehyde for the reasons above set forth, and the prior art does not teach a method for choosing a catalyst for obtaining glycol aldehyde from aqueous formaldehyde which will give a combination of high conversion rate, high selectivity to glycol aldehyde and good catalyst stability. Those in the art will recognize that high selectivity and high conversion may be all that are needed in a batch run; however good catalyst stability is also absolutely necessary in a commercial process wherein product is produced under continuous operating conditions. The inventor has unexpectedly discovered that to have the three qualities of high selectivity to glycol aldehyde, high conversion rate and good stability, the trialkylphosphine must have a cone angle within the range of 159 to 171.

The cone angle is a measure of steric properties of the phosphine. A very thorough discussion of cone angle can be found in the following publication: Chadwick A. Tolman, "Steric Effects of Phosphorus Ligands in Organometallic Chemistry and Homogeneous Catalysis", *Chemical Reviews*, 1977, Vol. 77, No. 3, pp. 313–348. All references in the Specification and the claims to "cone angle" are utilized in the Tolman article, and as such is measured in the Tolman article. As stated in the Tolman article the cone angle, in general terms, is the smallest angle of a cone (with its apex at a specified point in the phosphine ligand) which would contain all of the alkyl or cycloalkyl groups attached to the phosphorus atom.

Suitable trialkylphosphines and tricycloalkyl phosphines which have the proper cone angle are set forth in Table 1.

TABLE 1

| Phosphine | Cone Angle (Degrees) |
|---|---|
| Tricyclohexylphosphine | 170 |
| Tri-sec-butylphosphine | 160 |
| Tri-isopropylphosphine | 160 |

The especially preferred phosphine for use in the present invention is tricyclohexylphosphine.

The following Table 2 lists various triorganophosphines, and their respective cone angles which are not suitable for the present invention because their cone angle is not within the proper range. Also, two of the phosphines, di-tert-butylphenylphosphine and tribenzylphosphine, are not within the scope of the invention and not satisfactory for a catalyst because they include an aryl group, even though their cone angles are within the desired range.

TABLE 2

| Phosphines | Cone Angle (Degrees) |
|---|---|
| Di-tert-butylphenylphosphine | 170 |
| Tribenzylphosphine | 165 |
| Tri-tert-butylphosphine | 182 |
| Trimethylphosphine | 118 |
| Tri-n-butylphosphine | 132 |
| Triisobutylphosphine | 143 |
| Triphenylphosphine | 145 |
| Triphenylphosphite | 128 |

The hydroformylation reaction is preferably carried out in a solvent which will dissolve polar materials. Suitable solvents include a wide variety and are exemplified by N-substituted amides in which each hydrogen of the amido nitrogen is substituted by a hydrocarbon group, e.g., 1-methylpyrrolidin-2-one, N,N-dimethylacetamide, N,N-diethylacetamide, N-methylpiperidone, 1,5-dimethylpyrrolidin-2-one, 1-benzylpyrrolidin-2-one, N,N-dimethylpropionamide, hexamethylphosphoric triamide and similar such liquid amides; nitriles, such as acetonitrile, benzonitrile, propionitrile and the like; cyclic ethers such as tetrahydrofuran, dioxane and tetrahydropyran; ethers such as diethyl ether, 1,2-dimethyoxybenzene, alkyl ethers of alkylene glycols and polyalkylene glycols, e.g., methyl ethers of ethylene glycol, propylene glycol and di, tri- and tetraethylene glycols; ketones, such as acetone, methyl isobutyl ketone, and cyclohexanone; esters, such as ethyl acetate, ethyl propionate and methyl laurate; lactones of organic carboxylic acids, such as butyrolactone and valerolactone organic acids such as acetic acid, propionic acid and caproic acid; and alkanols, such as methanol, ethanol, propanol, 2-ethylhexanol and the like; and mixtures thereof. Many of the solvents are non-reactive in the medium whereas others are capable of functioning as ligands. The selected solvent should preferably be liquid under the reaction conditions.

The rhodium may be introduced into the reaction zone in any convenient manner. For example the rhodium salt of an organic acid may be combined with the ligands in the liquid phase and then subjected in the reaction zone to the synthesis gas. Alternatively, the catalyst can be prepared from a carbon monoxide complex of rhodium, such as hexarhodium hexadecacarbonyl, by heating such with the ligands. Also, and the method of choice, is to introduce into the reaction zone as a catalyst precursor, a rhodium complex such as the rhodium dicarbonyl complex formed with acetylacetonate ligand, and then introducing separately to the reaction zone the triorganophosphine ligand. The general method of forming similar catalysts is disclosed and discussed in various literature such as U.S. Pat. No. 4,484,006 issued Nov. 20, 1984 to Henry R. Menapace; U.S. Pat. No. 4,287,370 issued Sept. 1, 1981 to Norman Harris, et al; and in British Patent Specification 1,243,189 of Malcolm John Lawrenson, et al published Aug. 18, 1971. Other references to similar catalysts are in the article by B. Fell, et al, Tetrahedron Letters, 1968, pages 3261–3266; U.S. Pat. No. 4,260,828 issued Apr. 7, 1981 to Morrell, et al; U.S. Pat. No. 4,268,688 issued May 19, 1981 to Tinker, et al; U.S. Pat. No. 4,258,214 issued Mar. 24, 1981 to Bahrmann, et al; U.S. Pat. No. 3,965,192 issued June 22, 1976 to Frank B. Booth; European Patent Application Publication 0-080-449-A1 published June 1, 1983 to Monsanto Chemical Company; U.S. Pat. No. 3,239,566 issued Mar. 8, 1966 to Slaugh et al; and U.S. Pat. No. 4,482,749 issued Nov. 13, 1984 to Dennis et al.

The preferred catalyst for use in the invention is one of Formula I above which has been prepared utilizing a precursor consisting of a rhodium complex with a beta-diketone, such as the rhodium dicarbonyl complex formed with acetylacetonate ligand. The beta-diketone utilized for forming the complex may be any of those generally available. Suitable beta-diketones include acetylacetone, dibenzoylmethane, benzoylacetone, diprivaloylmethane, 3-alkyl-2,4-pentanedione, and 2-acetylcyclohexanone. Preferably the beta-diketone will be composed only of carbon, hydrogen and oxygen and will be free of ethylenic and acetylenic unsaturation. The especially preferred beta-diketone is acetylacetone.

The amount of catalyst employed in the hydroformylation reaction does not seem to be critical and may vary considerably. At least a catalytically effective amount of catalyst should be used, of course. In general, an amount of catalyst which is effective to provide a reasonable reaction rate is sufficient. As little as 0.001 mole of rhodium per liter of reaction medium can suffice while amounts in excess of 0.1 mole does not appear to materially affect the rate of reaction. For most purposes, the effective preferred amount of catalyst is in the range of from about 0.002 to about 0.025 mole per liter.

The selectivity for glycol aldehyde and the rate of reaction appears to change relative to the ratio of the amount of phosphine ligand to the amount of rhodium. Generally, it has been found that increasing the amount of phosphine ligand relative to the rhodium to greater than 1:1 dramatically increases the rate of reaction while simultaneously decreasing glycol aldehyde selectivity. The rate of formaldehyde hydroformylation and glycol aldehyde selectivity obtained using excess phosphine can be moderated by incorporating an acid into the reaction medium. Thus, it has been found that by adding phosphoric acid to a catalyst which has a ratio of tricyclohexylphosphine to rhodium of 4:1, the glycol aldehyde selectivity can approach glycol aldehyde selectivity obtained from a 1:1 ratio although, a substantial reduction in the rate of formaldehyde hydroformylation takes place.

The reaction conditions are not overly critical in that wide ranges of elevated temperatures and superatmospheric pressures are operable. The practical limitations of production equipment will dictate to a great extent the selection of temperatures and pressures in which the reaction is to be effected. Thus, using available production systems, the selected elevated temperature should be at least about 75° C., and can range up to about 200° C., and even higher. For most purposes, the preferred operating temperature ranges from about 75° C. to about 125° C. It has been found that an increase in reaction temperature from 100° C. to 150° C. results in an increase in the selectivity to methanol and ethylene glycol. Thus, it appears that the hydrogenation pathway is highly favored at 150° C. This suggests that the glycol aldehyde produced selectivity at lower temperatures such as 100° C. could be hydrogenated in situ with the same catalyst system in another reactor at the higher temperature. The superatmospheric pressure should be at least about 10 atmospheres and can range up to almost any pressure attainable with production apparatus. Since extremely high pressure apparatus is quite expensive, pressures to about 500 atmospheres are suggested. Most desirably, the pressure should be in the range of from about 100 to about 400 atmospheres, particularly when employing the aforesaid preferred temperature range. It has been found, however, that the glycol aldehyde selectivity decreases slightly as a result of decreasing the total pressure from about 225 atmospheres to 100 atmospheres. Lowering the total pressure to 500 psig (31 atmospheres) results in a substantial decrease in glycol aldehyde selectivity.

The reaction pressures represent the total pressure gases contained in the reactor, i.e., carbon monoxide and hydrogen, and, if present, any inert diluent gas such as nitrogen. As in any gaseous system, the total pressure is the sum of partials pressures of component gases. In the present reaction, the molar ratio of hydrogen to carbon monoxide can range from about 1:10 to about 10:1, with the preferred ratio, from about 1:5 to about 5:1, and the reaction pressure can be achieved by adjusting the pressure of these gases in the reactor. For best results, the molar ratio of carbon monoxide to hydrogen is maintained at high values where partial pressures of carbon monoxide favor production of glycol aldehyde. Thus, to produce glycol aldehyde, the partial pressure of carbon monoxide is usually adjusted to be about 3 to about 10 times that of hydrogen.

As with any process of this kind, the present process can be conducted in batch, semi-continuous, and continuous operation. The reactor should be constructed of materials which will withstand the temperatures and pressure required, and the internal surfaces of the reactor are substantially inert. The usual controls can be provided to permit control of the reaction such as heat exchangers and the like. The reactor should be provided with adequate means for agitating the reaction mixture; mixing can be induced by vibration, shaking, stirring, oscillation and the like methods.

The results obtained with the present process are surprising and totally unexpected. For the first time, substantial formaldehyde conversion and selectivity to glycol aldehyde can be achieved by hydroformylating aqueous formaldehyde. Thus, glycol aldehyde selectivities greater than 80% and even as high as 94% have been achieved with greater than 70% aqueous formaldehyde conversion. The remarkable results pertaining to the hydroformylation of aqueous formaldehyde are believed to be attributable to the catalytic complex which is utilized. Thus, the rhodium-phosphine ligand complex wherein the phosphine ligand is a triorgano phosphine which has a cone angle within the range of 159 to 171° results in conversion rates and glycol aldehyde selectivities thought only possible utilizing paraformaldehyde as the formaldehyde source.

The following examples further illustrate the invention.

The hydroformylation of aqueous formaldehyde was conducted to illustrate the present invention. All examples used the same formaldehyde source, catalyst and procedure.

A 50% aqueous formaldehyde solution was used as the formaldehyde source.

The catalyst system consisted of a Rh catalyst (Acetylacetonato-dicarbonylrhodium, $Rh(CO_2C_5H_7O_2)$, Engelhard) and a ligand tricyclohexylphosphine. The Rh catalyst had to be recrystallized before using it for the hydroformylation runs. The dark-red powder was dissolved in n-hexane (500-mls per 10.0g cat.) and heated to 60° C. The green solution was filtered hot through a heated funnel with filter paper. The filtrate was allowed to cool, producing fine needle crystals. Catalyst yields were 80% to 85%. This included concentrating the mother liquid at least twice. The ligand is air-sensitive and is weighted in a dry-bag under $N_2$.

A stirred 300-ml Hastelloy C autoclave was charged in the following order: Rh Catalyst, ligand, acid moderator (if used), and the solution of solvent and aqueous formaldehyde. The reactor was then sealed and purged 3 times with nitrogen. The mixture was allowed to stir for 20 minutes at 750 rpm. After the solution was stirred, the nitrogen was vented and the reactor filled to 100 psig less than actual reaction pressure. This allows the reactor contents to expand to near reaction pressure when heated. The reactor was then blocked-off and heated to reaction temperature. After the reactor contents had equilibrated, the needed amount of syngas was charged into the reactor. The temperature, pressure, and gas-uptake were monitored until all the formaldehyde had reacted with the $H_2/CO$ mixture. At completion, the heater was shut-off and the reactor vented when the temperature was 50° C. Gas samples were collected at this time and the product was transferred by a pipette into a storage bottle.

The starting formaldehyde solution was analyzed by a standard wet chemical method. The final product was analyzed by a gas chromatographic method.

EXAMPLE 1

Using the above described procedure, several runs were conducted utilizing what is believed to be preferred reaction conditions. The results are shown in Table 3.

As can be seen from Table 3, the hydroformylation of 50% aqueous formaldehyde yielded glycol aldehyde selectivities of greater than 85% and even greater than 90% nn most cases at temperatures of about 100° C. and pressures above 3500 psig. Conversions of the aqueous formaldehyde were far greater than 50% and even greater than 70%. It can be seen also, that for most of the samples, accountabilities of glycol aldehyde, ethylene glycol and methanol were 100%. This is important inasmuch as it illustrates that the present invention is able to convert a substantial amount of the aqueous formaldehyde to glycol aldehyde without the formation of sugar-like by-products.

TABLE 3

| | HYDROFORMYLATION RESULTS WITH 50% AQUEOUS FORMALDEHYDE | | | | | | | | |
|---|---|---|---|---|---|---|---|---|---|
| Run # | $Rh(CO)_2AcAc$ | | | | | | % Selectivity | | |
| Time (Hr) Acid | $P(C_6H_{11})_3$ Moderator | Temp (°C.) Press. (psig) | $H_2/CO$ solvent | $CH_2O$ Mole/l | % Conv. Kobs (1/mole* hr.) | | GA | EG Accountability | MeOH |
| 1 | 11.8 mM | 100 | 1:1 | 0.9 | 64 | | 89 | 2 | 9 |
| 4.0 | 11.8 mM | 3500 | tetraglyme | | 0.44 | | | 110% | |
| 2 | 12.3 mM | 100 | 1:1 | 1.2 | 72 | | 91 | 3 | 6 |
| 4.5 | 12.3 mM | 3600 | tetraglyme | | — | | | 93% | |
| 3 | 8.0 mM | 100 | 1:1 | 1.2 | 72 | | 94 | 0 | 6 |
| 4.0 | 8.0 mM | 2950 | tetraglyme | | — | | | 105% | |
| 4 | 8.4 mM | 103 | 1:4 | 1.2 | 63 | | 95 | 0.4 | 5 |
| 3.75 $H_3PO_4$ | 7.8 mM 4.2 mM | 4000 | tetraglyme | | 0.41 | | | 102% | |
| 5 | 8.0 mM | 100 | 2:1 | 1.3 | 52 | | 92 | 1 | 7 |
| 2.5 $H_3PO_4$ | 7.8 mM 11.4 mM | 4000 | tetraglyme | | 0.35 | | | 100% | |
| 6 | 9.0 mM | 95 | 2:1 | 1.2 | 53 | | 93 | 2 | 6 |
| 1.5 | 8.7 mM | 4500 | THF | | — | | | 111% | |
| 7 | 12.1 mM | 100 | 1:1 | 1.2 | 66 | | 89 | 3 | 8 |
| 3.5 | 12.5 mM | 3900 | tetraglyme | | — | | | 90% | |
| 8 | 12.0 mM | 100 | 1:2 | 1.2 | 76 | | 88 | 2 | 10 |
| 5.0 | 14.3 mM | 3900 | tetraglyme | | — | | | 111% | |

EXAMPLE 2

In this example, hydroformylation runs were conducted to primarily illustrate the difference in yields obtained by varying the reaction pressure from about 500 psi to 3600 psi. It can be seen from Table 4 that by lowering the reaction pressure, the selectivity to glycol aldehyde decreased. At 475 psig, glycol aldehyde selectivities of only 60% were achieved.

TABLE 4

| | HYDROFORMYLATION RESULTS WITH 50% AQUEOUS FORMALDEHYDE | | | | | | | | |
|---|---|---|---|---|---|---|---|---|---|
| Run # | $Rh(CO)_2AcAc$ | | | | | | % Selectivity | | |
| Time (Hr) Acid | $P(C_6H_{11})_3$ Moderator | Temp (°C.) Press. (psig) | $H_2/CO$ solvent | $CH_2O$ Mole/l | % Conv. Kobs (1/mole* hr.) | | GA | EG Accountability | MeOH |
| 9 | 12.4 mM | 100 | 1:1 | 1.2 | 72 | | 91 | 3 | 6 |
| 4.5 | 12.3 mM | 3600 | tetraglyme | | — | | | 91% | |

TABLE 4-continued

| Run # Time (Hr) Acid | Rh(CO)2AcAc P(C6H11)3 Moderator | Temp (°C.) Press. (psig) | H2/CO solvent | CH2O Mole/l | % Conv. Kobs (1/mole* hr.) | % Selectivity GA | EG Accountability | MeOH |
|---|---|---|---|---|---|---|---|---|
| 10 4.75 | 12.0 mM 12.0 mM | 101 3600 | 1:1 tetraglyme | 1.2 | 72 0.40 | 83 | 2 97% | 15 |
| 11 4.0 | 12.5 mM 13.2 mM | 100 1400 | 1:1 tetraglyme | 1.2 | 72 0.38 | 83 | 1 100% | 16 |
| 12 3.2 | 12.1 mM 11.7 mM | 98 475 | 1:1 tetraglyme | 1.2 | 65 0.52 | 60 | 1 99% | 39 |
| 13 1.0 | 12.4 mM 11.8 mM | 98 1500 | 1:1 tetraglyme | 0.90 | 45 0.45 | 82 | 1 100% | 17 |
| 14 4.0 | 11.8 mM 11.8 mM | 100 3500 | 1:1 tetraglyme | 0.90 | 64 0.44 | 89 | 2 109% | 9 |
| 15 4.0 | 12.6 mM 12.8 mM | 98 1500 | 1:1 tetraglyme | 2.90 | 79 0.30 | 82 | 1 85% | 17 |
| 16 4.0 | 40.0 mM 40.0 mM | 100 1500 | 1:1 tetraglyme | 1.20 | 63 0.83 | 76 | 1 96% | 23 |
| 17 13.0 | 4.0 mM 4.0 mM | 100 1500 | 1:1 tetraglyme | 1.20 | 74 0.21 | 73 | 1 90% | 26 |

50% Aqueous Formaldehyde was diluted to 20 Wt. % prior to use in Run #13.

EXAMPLE 3

Reaction temperature was varied from 100° to 150° C. to determine the affect of reaction temperature on formaldehyde conversion and glycol aldehyde selectivity. It can be seen in Table 5 that reaction temperatures of about 150° C. yielded substantially more ethylene glycol and methanol than glycol aldehyde. As stated above, this suggests that the hydrogenation reaction is preferred at the higher temperatures.

As can be seen in Table 6, Runs 25–32, the presence of water in the reaction medium greatly reduced the reaction selectivity to glycol aldehyde relative to the selectivity found using the catalyst complex of this invention. The results of Runs 25–32 can be compared with the glycol aldehyde selectivities of around 90% and better using the catalyst of the present invention illustrated in Runs 1–8 at Table 3.

Runs 33–34 also illustrate the effect of water on the

TABLE 5

| Run # Time (Hr) Acid | Rh(CO)2AcAc P(C6H11)3 Moderator | Temp (°C.) Press. (psig) | H2/CO solvent | CH2O Mole/l | % Conv. Kobs (1/mole* hr.) | % Selectivity GA | EG Accountability | MeOH |
|---|---|---|---|---|---|---|---|---|
| 18 3.0 | 8.0 mM 8.2 mM | 150 4500 | 2:1 tetraglyme | 1.2 | 99 — | 10 | 13 91% | 77 |
| 19 4.0 | 7.8 mM 7.8 mM | 155 4300 | 2:1 DMP | 0.28 | 86 — | 0 | 12 — | 71 |
| 20 2.75 | 7.8 mM 7.8 mM | 145 4800 | 2:1 DMP | 0.28 | 78 — | 10 | 24 — | 66 |
| 21 3.5 | 12.1 mM 12.5 mM | 100 3900 | 1:1 tetraglyme | 1.2 | 66 — | 89 | 3 90% % Yield 2 | 8 |
| | | | | | | 59 | 2 | 5 |
| 21 1.0 | 12.1 mM 12.5 mM | 147 3300 | 1:0 tetraglyme | — | 100 — | 7 | 52 87% | 41 |
| 23 5.0 | 12.0 mM 14.3 mM | 100 3900 | 1:2 tetraglyme | 1.2 | 76 — | 88 | 2 111% % Yield | 10 |
| | | | | | | 67 | 1 | 4 |
| 24 2.25 | 12.0 mM 14.3 mM | 140 3900 | 4:1 tetraglyme | — | 93 — | 46 | 27 92% % Yield | 27 |
| | | | | | | 43 | 25 | 25 |

EXAMPLE 4

This example illustrates comparative runs in which aqueous formaldehyde was hydroformylated in the presence of a rhodium-triphenylphosphine catalyst.

rhodium-triphenylphosphine catalyst in which minute amounts of the formaldehyde reactant were used. Thus, it can be seen that as the water content increases, greatly reduced selectivities to glycol aldehyde are obtained.

TABLE 6

| | HYDROFORMYLATION OF AQUEOUS FORMALDEHYDE USING Rh—TRIPHENYLPHOSPINE CATALYST | | | | | | | | | | | |
|---|---|---|---|---|---|---|---|---|---|---|---|---|
| Run # | Rh[PPh3] g | CH2O g | H2O g | DMF g | PRESSURE H2 | PSIG CO | CO/H2 | T °C. | T hr | % Conv. | % Selectivity GA | MeOH |
| 25 | 0.24 | 8.4992 | 9.2672 | 33.434 | 700 | 2800 | 4.0 | 100 | 2.0 | 84 | 12.3 | 11.2 |
| 26 | 0.24 | 7.8352 | 1.9588 | 39.176 | 700 | 2800 | 4.0 | 100 | 2.0 | 77.6 | 45.7 | 5.7 |
| 27 | 0.24 | 7.8336 | 1.9584 | 39.168 | 700 | 2800 | 4.0 | 100 | 5.0 | 99.3 | 8.9 | 3.8 |
| 28 | 0.24 | 8.7310 | 2.0150 | 40.915 | 500 | 2000 | 4.0 | 100 | 2.0 | 71.4 | 51.0 | 9.8 |

TABLE 6-continued

HYDROFORMYLATION OF AQUEOUS FORMALDEHYDE
USING Rh—TRIPHENYLPHOSPINE CATALYST

| Run # | Rh[PPh$_3$] g | CH$_2$O g | H$_2$O g | DMF g | PRESSURE PSIG H$_2$ | PSIG CO | CO/H$_2$ | T °C. | T hr | % Conv. | % Selectivity GA | MeOH |
|---|---|---|---|---|---|---|---|---|---|---|---|---|
| 29 | 0.24 | 8.5760 | 1.9620 | 39.762 | 500 | 2000 | 4.0 | 100 | 2.0 | 72.6 | 52.3 | 8.8 |
| 30 | 0.24 | 4.6448 | 1.1294 | 41.286 | 500 | 2000 | 4.0 | 100 | 5.0 | 91.5 | 36.2 | 5.5 |
| 31 | 0.24 | 7.8448 | 1.9612 | 39.224 | 700 | 2800 | 4.0 | 100 | 5.0 | 85.4 | 24.3 | 2.3 |
| 32 | 0.24 | 8.4245 | 9.1857 | 33.140 | 700 | 2800 | 4.0 | 100 | 2.0 | 95 | 0.6 | 5.2 |
| 33 | 0.22 | 0.8157 | 0.8860 | 45.183 | 700 | 2800 | 4.0 | 100 | 2.0 | 86 | 100.5 | 2.4 |
| 34 | 0.24 | 0.8733 | 2.7889 | 42.108 | 700 | 2780 | 4.0 | 100 | 2.0 | 97.9 | 63.3 | 5.1 |
| 35 | 0.24 | 0.8549 | 9.8920 | 34.018 | 700 | 2800 | 4.0 | 100 | 2.0 | 98.4 | 39.4 | 18.7 |

What is claimed is:

1. In a process for reacting formaldehyde, carbon monoxide and hydrogen in the presence of a rhodium complex catalyst under hydroformylation conditions to form glycol aldehyde, the improvement which comprises: using as said source of formaldehyde an aqueous formaldehyde solution and as said catalyst a complex of rhodium with a triorganophosphine ligand, wherein said triorganophosphine ligand is selected from the group consisting of trialkylphosphines and tricycloalkylphosphines, wherein each of the three alkyl and cycloalkyl groups are alike or different and each contains from 1 to 10 carbon atoms, said triorganophosphine ligand having a cone angle within the range of 159 to 171 degrees.

2. The improvement of claim 1 wherein said hydroformylation conditions include an elevated temperature of about 75° C. to about 200° C. and a reaction pressure of from about 10 atmospheres to about 500 atmospheres.

3. The improvement of claim 2 wherein said temperature ranges from about 75° C. to about 125° C.

4. The improvement of claim 2 wherein said reaction pressure comprises from about 1,400 psig to about 4,000 psig.

5. The improvement of claim 2 wherein said reaction temperature comprises from about 75° C. to about 125° C. and a reaction pressure of about 1,400 psig to about 4,000 psig.

6. The improvement of claim 1 wherein the mole ratio of phosphine ligand to rhodium is at least 1:1.

7. The improvement of claim 1 wherein said aqueous formaldehyde comprises 37 to 50% formaldehyde in water.

8. The improvement of claim 1 wherein said phosphine ligand comprises tricyclohexylphosphine.

9. The improvement of claim 7 wherein said phosphine ligand comprises tricyclohexylphosphine.

10. The improvement of claim 1 wherein said triorganophosphine ligand is tri-sec-butylphosphine.

11. The improvement of claim 1 wherein said triorganophosphine ligand is tri-isopropylphosphine.

12. In a process for reacting formaldehyde, carbon monoxide and hydrogen in the presence of a rhodium complex catalyst under hydroformylation conditions to form glycol aldehyde, the improvement which comprises: using as said source of formaldehyde an aqueous formaldehyde solution and as said catalyst rhodium complexed with tricycloalkylphosphine, and wherein said hydroformylation conditions include an elevated temperature of at least about 75° C. to about 200° C. and a reaction pressure of from about 10 atmospheres to about 500 atmospheres.

13. The improvement of claim 12 wherein said aqueous formaldehyde comprises 37 to 50% formaldehyde in water.

14. The improvement of claim 12 wherein said temperature ranges from about 75° C. to about 125° C.

15. The improvement of claim 12 wherein said reaction pressure comprises from about 1,400 psig to about 4,000 psig.

16. The improvement of claim 12 wherein said reaction temperature comprises from about 75° C. to 125° C. and a reaction pressure of about 1,400 psig to about 4,000 psig.

17. The improvement of claim 12 wherein the mole ratio of phosphine ligand to rhodium is at least 1:1.

18. The improvement of claim 12 wherein said aqueous formaldehyde solution is 50% formaldehyde in water.

19. The improvement of claim 17 wherein said mole ratio of phosphine ligand to rhodium is greater than 1:1.

20. The improvement of claim 19 including adding an acid modifier to said catalyst.

21. The improvement of claim 20 wherein said acid modifier is phosphoric acid.

22. The improvement of claim 13 wherein said reaction temperature comprises from about 75° C. to 125° C. and a reaction pressure of about 1,400 psig to about 4,000 psig.

* * * * *